United States Patent [19]
Dalton

[11] Patent Number: 5,499,976
[45] Date of Patent: Mar. 19, 1996

[54] CATHETER RETAINER

[76] Inventor: Michael J. Dalton, 9432 Monticello Ave., Evanston, Ill. 60203

[21] Appl. No.: 318,264

[22] Filed: Oct. 5, 1994

[51] Int. Cl.$^6$ .................................................. A61M 25/02
[52] U.S. Cl. .................... 604/180; 128/DIG. 26
[58] Field of Search .................... 604/174, 179, 604/180; 128/DIG. 26

[56] References Cited

U.S. PATENT DOCUMENTS

| | | | |
|---|---|---|---|
| 2,757,512 | 12/1955 | Muller | 604/180 |
| 3,568,679 | 3/1971 | Reif | 604/180 |
| 4,380,234 | 4/1983 | Kamen | 604/180 |
| 4,393,873 | 7/1983 | Nawash et al. | 604/180 |
| 4,533,349 | 8/1985 | Bark | 604/180 |
| 4,579,120 | 4/1986 | MacGregor | 604/174 |
| 4,867,154 | 9/1989 | Potter et al. | 604/180 |
| 4,976,698 | 12/1990 | Stokley | 604/180 |
| 4,981,475 | 1/1991 | Haindl | 604/174 |
| 5,112,312 | 5/1992 | Luther | 128/DIG. 26 |
| 5,147,320 | 9/1992 | Reynolds et al. | 604/180 |
| 5,167,639 | 12/1992 | Hollands et al. | 604/180 |
| 5,336,195 | 8/1994 | Daneshvar | 604/179 |

*Primary Examiner*—Paul J. Hirsch
*Attorney, Agent, or Firm*—Richard L. Hansen

[57] ABSTRACT

A catheter retainer which includes a flexible flattened pad, a tunnel sized to pass the catheter extending transversely through the pad and a slit on the back face of the pad, following the tunnel, for insertion of the catheter, together with a method for using the catheter retainer.

20 Claims, 3 Drawing Sheets

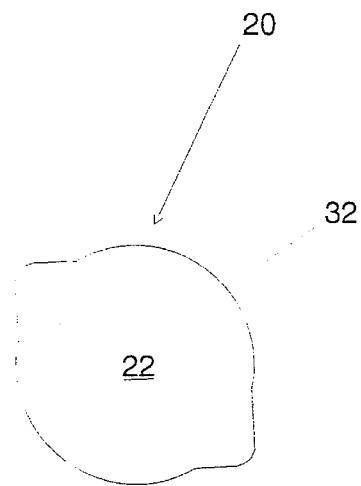
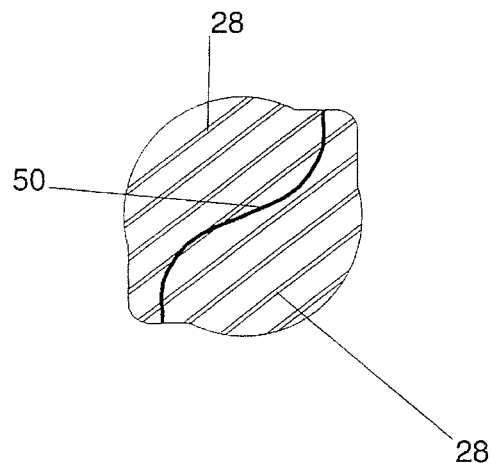
Fig. 1
Fig. 2
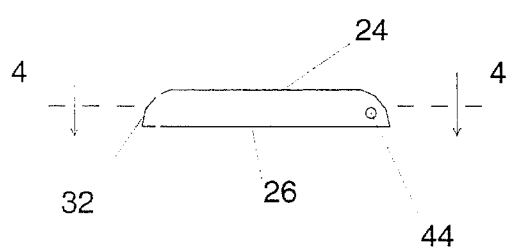
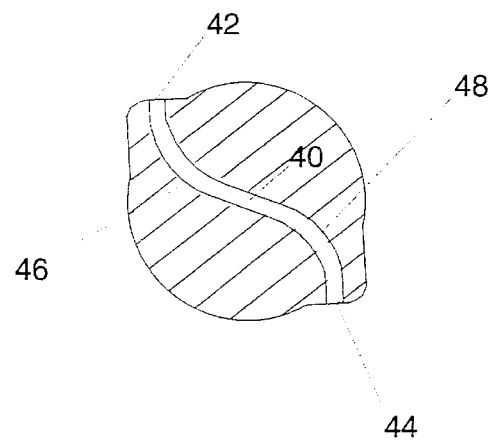
Fig. 3
Fig. 4

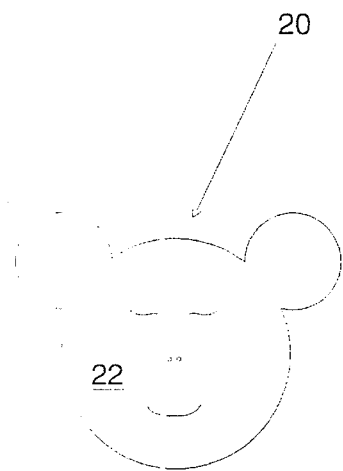
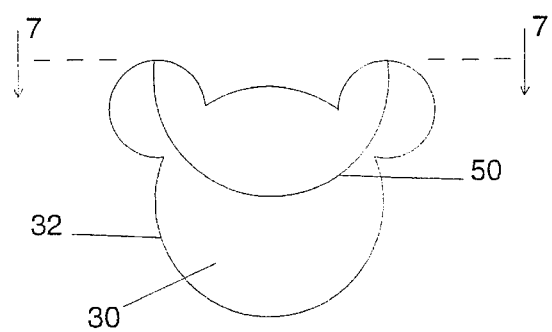
Fig. 6
Fig. 7
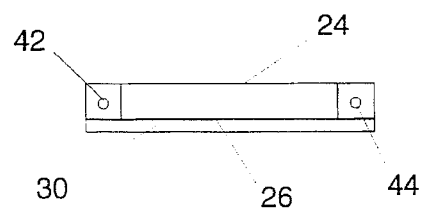
Fig. 8

CATHETER RETAINER

This invention is in the field of medical devices, particularly catheters for delivering a fluid into or out of the body. More specifically, this invention relates to means for retaining a catheter on the surface of the skin.

BACKGROUND

With the rapid advance of medical science, an increasing number of therapies for the treatment of disease involve the implantation of a mechanical device for the delivery of a fluid to a specific site within the body or the receipt of a fluid from a specific site within the body over a prolonged period of time. In some cases the implanted medical device is a drug infusion port which delivers medication to, for example, a cancerous tumor. In these cases the infusion port can be connected to a drug supply which is external to the body via a transdermal catheter. In other cases, an external drug infusion pump is connected to a catheter led through the skin to the internal site where medication is needed.

In other types of medical procedures, such as intravenous feeding, angioplasty and in the administration of an anesthetic, for example, a catheter can be led across the skin to a site where transdermal access is achieved. In all of the aforecited and similar situations it is important that the catheter be anchored to the surface of the skin and protected in such a way that it cannot accidentally be pulled out of the body. If the catheter is pulled out it may require a surgical operation to replace it.

Consequently, in the aforecited and similar situations it is a standard practice to anchor the catheter externally on the skin by means of adhesive tape or an occlusive dressing. In the course of placing and replacing such means for anchoring the catheter, adhesive particles, threads, dirt and other debris is transferred to the surface of the catheter. This makes for an unsanitary and generally unsatisfactory condition.

SUMMARY OF THE INVENTION

It is to the prevention of the aforesaid condition that this invention is directed.

Thus, it is one object of this invention to provide means for retaining a catheter securely on the surface of the body which protects the catheter against the accumulation of dirt and debris on its surface. It is another objective of this invention to provide a catheter retainer which is simple and inexpensive to produce as well as easy to use.

Consequently, this invention provides a catheter retainer which includes a flexible, flattened pad to be placed against the skin. The pad has a tunnel which extends through the pad transversely from one opening on the edge of the pad to another opening on the edge of the pad. The tunnel is sized to pass the catheter. An access slit on the back face of the pad follows the tunnel.

The catheter retainer is used by folding the catheter retainer from the back face toward the top face, opening the slit and exposing the tunnel. The catheter is then laid in the tunnel, and the pad is flattened again, thereby retaining the catheter. The catheter retainer is then affixed to the skin using adhesive means which contacts the retainer, not the catheter.

The invention, including the manner and means by which it can be used will be clarified by reference to the drawings which accompany this specification and to the detailed description which follows.

BRIEF DESCRIPTION OF THE DRAWINGS

FIG. 1 is a top plan view of one embodiment of the catheter retainer of this invention.

FIG. 2 is a bottom view of the catheter retainer of FIG. 1.

FIG. 3 is an edge view of the catheter retainer of FIG. 1.

FIG. 4 is a sectional view taken along line 4—4 in FIG. 3.

FIG. 6 is a top plan view of another embodiment of the catheter retainer of this invention.

FIG. 7 is a back view of the catheter retainer of FIG. 6.

FIG. 8 is an edge view taken along line 7—7 in FIG. 7.

DETAILED DESCRIPTION

Figure 5:
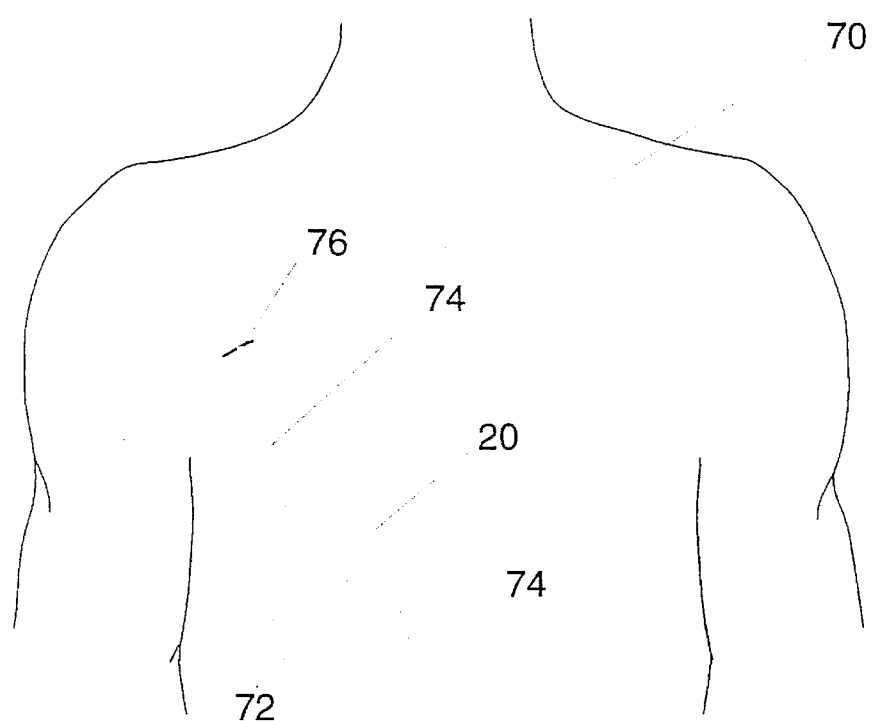
FIG. 5 is a diagrammatic view of a portion of a human body having an externalized catheter affixed to the body using a catheter retainer of this invention.

With reference now to FIGS. 1–4, catheter retainer 20 includes flattened pad 22, access tunnel 40 and slit 50. Pad 22 is made of a material which is flexible. Suitable flexible materials include, for example, thickened paper products, such as cardboard, and thickened woven, nonwoven, braided or knitted textile products, any of which may contain one or more natural or synthetic resins to consolidate and stiffen the fibers. Other suitable flexible materials are certain relatively inelastic synthetic plastic materials, such as high or low density polyethylene, polyvinyl chloride, etc.

In preferred embodiments of the invention the pad is not only flexible, it is also elastic. Suitable flexible, elastomeric materials include, for example, polyisoprene, poly(styrene-co-butadiene), polyisobutylene, polychloroprene, poly(butadiene-co-acrylonitrile), polysulfide, polyurethane, polyacrylate, polysiloxane and poly(fluorovinylsilane). Among these materials, polyurethane, polyacrylate and polysiloxane rubbers are preferred, and polysiloxane, or silicone, rubbers are especially attractive.

Readily available silicone rubber products which can be advantageously employed in the invention are SILASTIC brand silicone elastomer products and materials which can be obtained from Dow-Corning Corporation, Midland, Mich. More specifically, copolymers of dimethyl and methylvinyl siloxane, which may contain silica reinforcement, as well as pigment or dye to make them colored, can be used. A specific example is Dow-Corning SILASTIC Q7-4790 Medical Grade ETR Elastomer, a two-part product from which molded castings can be made.

The size of the pad is not a critical factor, except to the extent that size affects function and cost. The pad must be at least slightly thicker from top to bottom than the catheter it is designed to retain and large enough in area to facilitate anchoring it with adhesive means. The catheter retainer can, for example, range in thickness to accommodate a specific catheter; e.g., a Hickman size catheter having an O.D. of 0.125 in. or a Bioviac catheter having an O.D. of 0.090 in. A catheter retainer with a face area of about 1 in$^2$ may be large enough in some instances, but a greater area, up to about 3–4 in$^2$ may be indicated, depending upon, not only the size of the catheter, but also the location of the retainer on the body and the forces applied to it.

If the catheter retainer is to be made of a flexible but relatively inelastic material, pad 22 can be produced by die-cutting a stock sheet material, for example. Tunnel 40 can be introduced by drilling or pressing a bit, rod or tube through the material, and access slit 50 can be introduced by slitting through the back face of the pad. However, it is preferred that the catheter retainer be made in a mold.

The pad 22 is conveniently made by casting a melt or high solids solution of a flexible plastic, such as polyethylene into a mold. Preferably, however, a resin such as a silicon elastomer referred to above, or other two-part systems, such as polyurethane, can also be effectively employed. The liquid resin or resin precursor is simply poured into a mold of the desired shape and dimensions. Tunnel 40, generally round, can be created in the molding by including in the mold an appropriately sized and shaped removable tube or rod to which the resin does not adhere, such as stainless steel, for example. Slit 50 can be created after the resin solidifies by simply slitting the back face along the tunnel, freeing the means used to create it.

Tunnel 40 should be sized in cross section to retain the catheter. Preferably, at least a part of tunnel 40 should be sized in cross section no larger than the cross section of the catheter to be retained. In preferred embodiments, especially when the pad is not only flexible, but also elastic, at least part of the tunnel can be sized in cross section slightly smaller than the catheter to be retained. The cross section of the tunnel is one of the variable parameters which can be adjusted to retain the catheter to the desired degree.

The second parameter which can be adjusted to provide the degree of retention desired is the provision of one or more turns in the tunnel as it traverses the pad. Although a turn in the tunnel is not a requirement, one or more turns increase the frictional retention of the catheter in the retainer. However, a sharp turn in the catheter is to be avoided, since a sharp turn can cause a flow-restricting kink in the catheter. In general, the smaller in diameter the catheter is, the smaller the radius of the turn can be. In the catheter retainer of FIGS. 1–4, tunnel 40 begins with opening 42 at one point on edge 32 and includes a first turn 46 and a second turn 48 before terminating at opening 44; i.e, the tunnel is S-shaped.

Although not required, it is preferred that the top face of pad 22 be sloped or rounded from top face 24 toward back face 26 near edge 32. This helps to prevent "tenting" of an adhesive tape or pad applied over the catheter retainer to hold it in place on the skin. Another optional feature is the provision of grooves 28 on back face 26 to carry perspiration away from the undersurface of the pad.

With reference now to FIG. 5, catheter 74 accesses body 70 through an incision 76. The catheter is led through a catheter retainer 20 of this invention. The catheter retainer in then anchored to the skin with adhesive means, such as adhesive tape 72.

An alternative embodiment of this invention is illustrated in FIGS. 6–8, in which the various elements are labeled in the same way as they are in the embodiment of FIGS. 1–4. This embodiment is shaped in a way which invites decoration; e.g., as shown. In this alternative embodiment tunnel 50 makes a single turn and is C-shaped. Although in many cases it will be desired to anchor the catheter retainer on the skin using adhesive means which consist solely of an adhesive tape or pad, it may be desirable to avoid the adhesive tape or pad, or to augment it, by optionally providing an adhesive coating 30 on the back face 26 of pad 22. The thickness of the adhesive coating is exaggerated in FIG. 8.

While this invention is described with reference to two specific embodiments, it is not the intent that this invention be limited to those embodiments. Rather, the invention is limited only by the following claims:

I claim:

1. A one-piece catheter retainer which comprises
   (a) a flexible, flat pad of substantially uniform thickness having a smooth top face, a smooth back face and an edge;
   (b) a round tunnel sized to pass the catheter and extending completely inside the pad from a first opening on the edge to a second opening on the edge; together with
   (c) a normally closed access slit connecting the entire length of said tunnel to the back face of the pad, thereby permitting the catheter to be inserted and retained in the pad.

2. The catheter retainer of claim 1 wherein the tunnel makes at least one turn.

3. The catheter retainer of claim 2 wherein the tunnel makes one turn and is C-shaped.

4. The catheter retainer of claim 2 wherein the tunnel makes two turns and is S-shaped.

5. The catheter retainer of claim 1 wherein the pad is also elastic.

6. The catheter retainer of claim 1 wherein at least a part of the tunnel is sized no larger in cross section than the catheter cross section.

7. The catheter retainer of claim 1 wherein at least a part of the tunnel is sized smaller in cross section than the catheter cross section.

8. The catheter retainer of claim 1 wherein the back face of the pad carries grooves to transport perspiration.

9. The catheter retainer of claim 8 wherein said back face carries an adhesive.

10. A one-piece catheter retainer which comprises
    (a) a flexible, elastic, flat pad of substantially uniform thickness having a smooth top face, a smooth back face and an edge, said back face being rounded toward the back face at the edge, said back face carrying grooves to transport perspiration;
    (b) a round tunnel sized to pass the catheter and extending completely inside the pad, making an S-shaped turn, from a first opening on the edge to a second opening on the edge; together with
    (c) A normally closed access slit connecting the entire length of said tunnel to the back face of the pad, thereby permitting the catheter to be inserted and retained in the pad.

11. The catheter retainer of claim 10 wherein said back face carries an adhesive.

12. A method for retaining a catheter on the surface of a body which comprises
    (1) providing a catheter retainer which comprises
        (a) a flexible, flat pad of substantially uniform thickness having a smooth top face, a smooth back face and an edge;
        (b) a round tunnel sized to pass the catheter and extending completely inside the pad from a first opening on the edge to a second opening on the edge; together with
        (c) a normally closed access slit connecting the entire length of said tunnel to the back face of the pad;
    (2) folding the catheter retainer from back face to top face to open the slit and expose the tunnel;
    (3) inserting the catheter in the tunnel;
    (4) releasing the fold to flatten the catheter retainer; and then
    (5) anchoring the catheter retainer to the body by means of an adhesive.

13. The method of claim 12 wherein said adhesive is provided by adhesive tape.

14. The method of claim 12 wherein the tunnel makes one turn and is C-shaped.

15. The method of claim 12 wherein the tunnel makes two turns and is S-shaped.

16. The method of claim 12 wherein the pad is elastic.

17. The method of claim 12 wherein at least a part of the tunnel is sized no larger in cross section than the catheter cross section.

18. The method of claim 12 wherein at least a part of the tunnel is sized smaller in cross section than the catheter cross section.

19. The method of claim 12 wherein the back face of the pad carries grooves to transport perspiration.

20. The method of claim 19 wherein said back face carries an adhesive.

* * * * *